United States Patent [19]
Ellis et al.

[11] Patent Number: 5,981,572
[45] Date of Patent: Nov. 9, 1999

[54] BENZOFURANS AND BENZOPYRANS AS CHRONOBIOLOGICAL AGENTS

[75] Inventors: Frank Ellis; Terence Aaron Panchal; Peter Charles North, all of Stevenage; Jason William Beames Cooke, Royston; Simon Charles Dolan, Ricfmansworth, all of United Kingdom

[73] Assignee: Glaxo Wellcome Inc., Research Triangle Park, N.C.

[21] Appl. No.: 09/180,441

[22] PCT Filed: May 13, 1997

[86] PCT No.: PCT/EP97/02402

§ 371 Date: Nov. 6, 1998

§ 102(e) Date: Nov. 6, 1998

[87] PCT Pub. No.: WO97/43272

PCT Pub. Date: Nov. 20, 1997

[30] Foreign Application Priority Data

May 14, 1996 [GB] United Kingdom .................... 9610032
Nov. 15, 1996 [GB] United Kingdom .................... 9623775

[51] Int. Cl.$^6$ .......................... A61K 31/34; A61K 31/35; C07D 311/04; C07D 307/79
[52] U.S. Cl. .......................... 514/456; 514/469; 549/396; 549/462
[58] Field of Search ................... 549/396, 462; 514/456, 469

[56] References Cited

FOREIGN PATENT DOCUMENTS 0042299A 12/1981 European Pat. Off. .
WO 92/17464 10/1992 WIPO .
WO 93/12754 7/1993 WIPO .

OTHER PUBLICATIONS

Shen et al, "Structure–Actiivty Relationships for Substrates and Inhibitors of Pineal 5–Hydroxytryptamine–N–Acetyl-transferase:Preliminary Studies", European Journal of Pharmacology 307 (1996) 133–140.

Semmelhack et al, "New Substitution Reactions on Indole Promoted by the Cr(CO)$_3$ Unit", Journal of Organometallic Chemistry, 240 (1982) C5–C10.

Benassi et al, "Conformational Analysis of Organic Carbonyl Compounds. Part4.$^{1-3}$A $^1$H and $^{13}$C Nuclear Magnetic Resonance Study of Formyl and Acetyle Derivatives of Benzo[b]furan", J. Chem. Soc. Perkin Trans. 2, No. 9, 1984, pp. 1479–1485.

Dorta et al, Serendipitous Acid–Catalyzed Rearrangement of 13–Methoxyl–1,6,8.–trioxadispiro [4.1.5.3] pen tradecane to 3–Chroman–5–yl–1–o1, J. Org. Chem., vol. 62, No. 7, 1997, pp. 2273–2274.

Ecker et al, "Improved Synthesis and Pharmacologic Activity of the Enantiomers of a New Benzofurance type Anti-arrhythmic Compound", Chirality, vol. 6, No. 4, 1994, pp. 329–336.

Ecker et al, "Synthese unde Pharmakodynamische Aktivitat von 2–(3–(2–Phenylethyl) benzofuran–2–yl)–N–propylethanamin", Arch.Pharm. (Weinheim, Ger.), vol. 328, No. 4, 1995, pp. 343–348.

*Primary Examiner*—Laura L. Stockton
*Attorney, Agent, or Firm*—Nixon & Vanderhye

[57] ABSTRACT

The invention thus provides compounds of Formula (I)

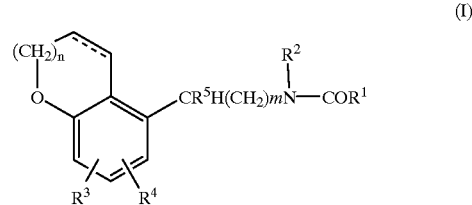

(I)

wherein $R^1$ and $R^2$ which may be the same or different represent H, $C_{1-6}$ alkyl or substituted alkyl or $C_{3-7}$ cycloalkyl; or aryl;

$R^3$, and $R^4$ which may be the same or different represent H, halogen, $C_{1-6}$ alkyl; or substituted aryl;

$R^5$ is H or $C_{1-6}$ alkyl;

n is an integer 0, 1 or 2 and m is an integer 1, 2, 3, or 4;

the dotted line indicates the presence or absence of an additional bond; and pharmaceutically acceptable solvates (e.g. hydrates) thereof.

16 Claims, No Drawings

BENZOFURANS AND BENZOPYRANS AS CHRONOBIOLOGICAL AGENTS

This application is a 371 of PCT/EP97/02402 filed May 13, 1997.

This invention relates to bicyclic compounds, to processes for their preparation, to pharmaceutical compositions containing them and to their medical use.

The invention thus provides compounds of Formula (I)

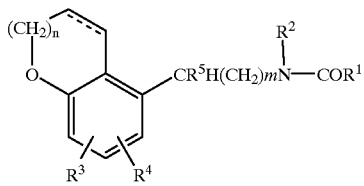

(I)

wherein $R^1$ and $R^2$ which may be the same or different represent H, $C_{1-6}$ alkyl or substituted alkyl or $C_{3-7}$ cycloalkyl; or aryl;

$R^3$, and $R^4$ which may be the same or different represent H, halogen, $C_{1-6}$ alkyl; or substituted aryl;

$R^5$ is H or $C_{1-6}$ alkyl;

n is an integer 0, 1 or 2 and m is an integer 1, 2, 3, or 4;

the dotted line indicates the presence or absence of an additional bond; and pharmaceutically acceptable solvates (e.g. hydrates) thereof.

It will be appreciated that in formula (I) hereinabove the substituents $R^3$ and $R^4$ may be attached at any available position on the phenyl portion of the bicyclic system. Preferably when n is 0, $R^3$ and $R^4$ are substituted in the 5 and/or 7 positions on the phenyl ring.

As used herein, an alkyl group may be a straight chain or branched chain alkyl group. Examples of suitable alkyl groups include $C_{1-4}$ alkyl groups, for example methyl, ethyl, n-propyl and isopropyl groups. When optionally substituted, the substituent is one or more fluorine atoms.

A halogen substituent may be fluorine, chlorine, bromine or iodine.

As used herein, the term "aryl" as a group means phenyl, optionally substituted by one or more (eg 1–3) atoms or groups selected from $C_{1-6}$ alkyl, $C_{1-6}$ alkoxy, hydroxyl, halogen, nitro and trifluoromethyl.

Cycloalkyl groups may be bridged cycloalkyl groups, eg norbornyl or non-bridged cycloalkyl groups, eg cyclopropyl.

Examples of the groups $R^3$ and $R^4$ include hydrogen, halogen (e.g. chlorine and/or fluorine) and $C_{1-3}$alkyl (e.g. methyl).

m preferably represents 2.

n preferably represents 0.

$R^2$ may particularly represent hydrogen or $C_{1-3}$alkyl (e.g. methyl).

$R^1$ may particularly represent hydrogen, $C_{3-5}$alkyl (i.e. methyl, ethyl, n-propyl or i-propyl) or $C_{3-5}$cycloalkyl (e.g. cyclopropyl or cyclobutyl).

A particular group of compounds of the invention are compounds of formula (1a).

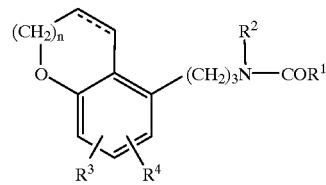

(1a)

and pharmaceutically acceptable solvates (e.g. hydrates) thereof, wherein $R^1$, $R^2$, $R^3$, and $R^4$ are as defined hereinabove especially halogen, more especially $R^3$ and $R^4$ are chlorine and/or fluorine, especially where $R^1$ is methyl or cyclopropyl.

Another particular group of compounds of the invention are compounds of formula 1(b)

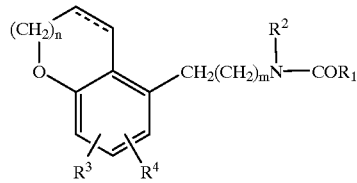

(1b)

wherein $R^1$ and $R^2$ which may be the same or different represent H, $C_{1-6}$ alkyl or substituted alkyl, $C_{3-7}$ cycloalkyl or aryl;

$R^3$, and $R^4$ which may be the same or different represent H, halogen, $C_{1-6}$ alkyl or substituted aryl;

n is an integer 0 or 1 and m is an integer 1, 2, 3, or 4;

the dotted line indicates the presence or absence of an additional bond; and pharmaceutically acceptable solvates (e.g. hydrates) thereof.

A further particular group of compounds are compounds of formula 1(c)

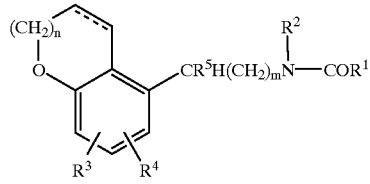

(1c)

wherein $R^1$ and $R^2$ which may be the same or different represent H, $C_{1-6}$ alkyl or $C_{3-7}$ cycloalkyl;

$R^3$, and $R^4$ which may be the same or different represent H, halogen, or $C_{1-6}$ alkyl;

$R^5$ is H or $C_{1-6}$ alkyl;

n is an integer 0, or 1 and m is an integer 1, 2, 3, or 4;

the dotted line indicates the presence or absence of an additional bond; and pharmaceutically acceptable solvates (e.g. hydrates) thereof.

Particular compounds according to the present invention include

N-[3-(2,3-dihydro-benzofuran-4-yl)-propyl]acetamide,

Cyclopropanecarboxylic acid -[3-(2,3-dihydro-benzofuran-4-yl)-propyl]-amide,

Cyclopropanecarboxylic acid -[3-(5-chloro-2,3-dihydro-benzofuran-4-yl)propyl]amide, Cyclopropanecarboxylic acid -[3-(5-chloro-7-fluoro-2,3-dihydro-benzofuran-4-yl)propyl]-amide, Cyclopropanecarboxylic acid [3-(5-chloro-7-fluoro-benzofuran-4-yl)-propyl]-amide, Cyclopropanecarboxylic acid -[3-benzofuran-4-yl)-propyl]-amide, Cyclopropanecarboxylic acid (3-chroman-5-yl-propyl)-amide, N-[3-(2,3-dihydro-5-fluorobenzofuran-4-yl)propyl] acetamide, Cyclopropanecarboxylic acid [3-(2,3-dihydro-5-fluoro-benzofuran-4-yl)propyl]amide.

It is to be understood that the present invention covers all combinations of particular and preferred groups described hereinabove.

References hereinafter to a compound of formula (I) includes the compound and its pharmaceutically acceptable solvates.

The compounds of formula (I) may contain at least one asymmetric carbon atom and may exist as stereoisomers. The compounds of formula (I) thus include the R- and S-isomers and mixtures, for example racemic mixtures, thereof.

The compounds of formula (I) have a high affinity and selectivity for binding to melatonin receptors and have either melatonin agonist or antagonist activity as demonstrated in cloned human ML1 receptors in Chinese hamster ovary cells. Accordingly, the compounds are of use as scientific tools for studying the role of melatonin within biological systems.

The compounds of formula (I) are also of use in the treatment of disorders which arise from a disturbed functioning of systems which are regulated by melatonin. In particular the compounds of formula (I) may be used in the treatment of chronobiological disorders, especially in the elderly population, glaucoma, cancer, psychiatric disorders, neurodegenerative diseases or neuroendocrine disorders arising as a result of or influenced by the systems which are regulated by melatonin.

Chronobiological disorders include seasonal affective disorders (SAD), primary and secondary insomnia disorders, primary and secondary hypersomnia disorders, sleep-wake schedule disorders (including advanced phase type, delayed phase type, disorganised type and frequently-changing type) and other dyssomnias, especially those caused by ageing, dementias, blindness, shift work and by rapid time-zone travel, commonly known as jet lag. Cancers which may be treated with a compound of formula (I) include solid tumours, e.g. melanomas and breast carcinomas.

Psychiatric disorders which may be related to altered melatonin function or influenced by melatonin and circadian rhythms include mood disorders (including bipolar disorders of all types, major depression, dysthymia and other depressive disorders), psychoactive substance dependence and abuse, anxiety disorders (including panic disorder, agoraphobia, social phobia, simple phobia, obsessive-compulsive disorder, post-traumatic stress disorder and generalised anxiety disorder), schizophrenia, epilepsy and epileptic seizures (including grand mal, petit mat, myoclonic epilepsy and partial seizures), disorders of involuntary movement (including those due to Parkinson's disease, and drug-induced involuntary movements) and dementias (including primary degenerative dementia of the Alzheimer type).

Neurodegenerative diseases which may be related to altered melatonin function or influenced by melatonin and biological rhythms include multiple sclerosis and stroke.

Neuroendocrine disorders which may be related to altered melatonin function or influenced by melatonin and biological rhythms include peptic ulceration, emesis, psoriasis, benign prostatic hyperplasia, hair condition and body weight. Particular neuroendocrine disorders which may be treated include those relating to the regulation of reproductive maturation and function include idiopathic delayed puberty, sudden infant death, premature labour, infertility, antifertility, premenstrual syndrome (including late luteal phase dysphoric disorder) and sexual dysfunction (including sexual desire disorders, male erectile disorder, post-menopausal disorders and orgasm disorders). The compounds may also be used to manipulate breeding cycles, body weight, coat colour and oviposition of susceptible hosts, including birds, insects and mammals. The compounds of formula (I) may also have sedative and analgesic effects, effects on the microcirculation and immunomodulant effects and may be useful for the treatment of hypertension, migraine, cluster headache, regulation of appetite and in the treatment of eating disorders such as obesity, anorexia nervosa and bulimia nervosa.

There is thus provided in a further aspect of the invention a compound of formula (I) for use in therapy, in particular in human medicine. It will be appreciated that use in therapy embraces but is not necessarily limited to use of a compound of formula (I) as an active therapeutic substance.

There is also provided as another aspect of the invention a compound of formula (I) for use in the preparation of a medicament for use in the treatment of conditions associated with a disturbed functioning of the melatonin system.

In an alternative or further aspect of the invention there is provided a method for the treatment of a mammal, including man, comprising administration of an effective amount of a compound of formula (I), in particular for the treatment of conditions associated with a disturbed functioning of the melatonin system.

It will be appreciated by those skilled in the art that reference herein to therapy and treatment extends to prophylaxis as well as the treatment of established symptoms.

While it is possible that, for use in therapy, a compound of formula (I) may be administered as the raw chemical it is preferable to present the active ingredient as a pharmaceutical formulation.

The invention thus further provides a pharmaceutical formulation comprising a compound of formula (1) together with one or more pharmaceutically acceptable carriers therefor. The carrier(s) must be 'acceptable' in the sense of being compatible with the other ingredients of the formulation and not deleterious to the recipient thereof.

Pharmaceutical formulations include those suitable for oral, rectal, vaginal, nasal, topical or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl-p-hydroxybenzoates or sorbic acid).

For topical administration in the mouth, the compositions may take the form of buccal or sub-lingual tablets, drops or lozenges formulated in conventional manner.

For topical administration to the epidermis the compounds may be formulated as creams, gels, ointments or lotions or as a transdermal patch. Such compositions may for example be formulated with an aqueous or oily base with the addition of suitable thickening, gelling, emulsifying, stabilising, dispersing, suspending and/or colouring agents.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glyceride.

Pessaries for vaginal administration may be formulated in a similar manner.

For intranasal administration the compounds of the invention may be used, for example, as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. 1,1,1, 2-trifluoroethane (HFA 134A) and 1,1,1,2,3,3,3-heptafluoropropane (HFA 227), carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Any of the pharmaceutical compositions described above may be presented in a conventional manner associated with controlled release forms.

The active ingredient may conveniently be presented in unit dose form. A convenient unit dose formulation contains the active ingredient in an amount of from about 0.1 mg to about 200 mg.

It will be appreciated that the precise dose administered will depend on the age and condition of the patient, the particular compound used and the frequency and route of administration and will ultimately be at the discretion of the attendant physician. The compound may be administered in single or divided doses and may be administered one or more times, for example 1 to 4 times per day.

A proposed dose of the compounds of the invention for oral, rectal, vaginal, intranasal, topical or parenteral administration to humans (of approximately 70kg bodyweight) for the treatment of conditions associated with a disturbed functioning of systems which are regulated by melatonin is 0.01 to 200 mg of the active ingredient per unit dose which could be administered, for example, 1 to 4 times per day.

For oral administration a unit dose will preferably contain from 0.1 to 200 mg of the active ingredient. A unit dose for parenteral administration will preferably contain 0.1 to 5 mg of the active ingredient.

Aerosol formulations are preferably arranged so that each metered dose or 'puff' delivered from a pressurised aerosol contains 0.2 mg to 2 mg of a compound of the invention, and capsules and cartridges delivered from an insufflator or an inhaler, contain 0.2 mg to 20 mg of a compound of the invention. The overall daily dose by inhalation with an aerosol will be within the range 0.2 mg to 100 mg. Administration may be once or several times daily, for example from 1 to 8 times, giving for example 1, 2 or 3 doses each time.

Dosages of the compounds of the invention for rectal, vaginal, intranasal or topical administration are similar to those for oral administration.

The compounds of the invention may, if desired, be administered in combination with one or more other therapeutic agents such as a hypnotic or antidepressant agent, or an anti-cancer agent such as tamoxiphen, or in combination with radiation therapy to treat cancer.

The combinations referred to above may conveniently be presented for use in the form of a pharmaceutical formulation and thus pharmaceutical formulations comprising a compound of formula (I) together with at least one other therapeutic agent and one or more pharmaceutically acceptable carriers therefore comprise a further aspect of the invention.

When compounds of formula (I) are used in combination with other therapeutic agents, the compounds may be administered either sequentially or simultaneously by any convenient route.

When such combinations are employed, the dose of each component of the combination will in general be that employed for each component when used alone.

Compounds of formula (I) and pharmaceutically acceptable solvates (e.g. hydrates) thereof, may be prepared by methods known in the art for the preparation of analogous compounds. In particular the compounds of formula (I) may be prepared by the methods outlined below and which form a further aspect of the invention. In the following processes, $R^1$, $R^2$, $R^3$, $R^4$, $R^5$ n and m unless stated otherwise, are as defined above for formula (I).

According to one general process (A) a compound of formula (I) may be prepared by acylation of a compound of formula (II),

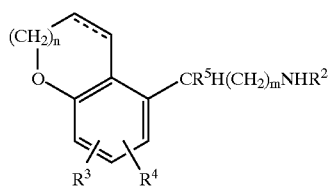
(II)

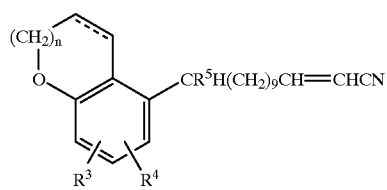
(IIIb)

Suitable acylating agents which may conveniently be used in the above process include acid anhydrides and acid halides. The reaction is conveniently effected in a suitable solvent such as an ether (e.g. diethyl ether, tetrahydrofuran or dioxan), a hydrocarbon such as toluene or a halogenated hydrocarbon (e.g. dichloromethane), esters (e.g. ethylacetate) preferably in the presence of a base such as pyridine or a tertiary amine (e.g. triethylamine), at a temperature in the range of 0 to 100° C., preferably 0 to 20° C.

The compounds of formula (I) thus produced wherein the dotted line represents an extra bond may be converted into the corresponding compound wherein the dotted line does not represent an extra bond by hydrogenation, for example hydrogenating the compound in ethanol over a transition metal catalyst eg rhodium which is then removed eg by filtration and the compound then subjected to further purification techniques.

Compounds of formula (II) in which $R^2$ is hydrogen and the dotted line represents a bond may conveniently be prepared by the reduction of compounds of formula (III).

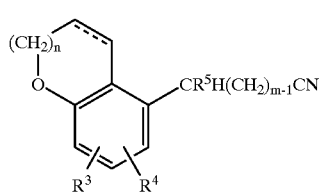
(III)

The reduction may conveniently be effected using a reducing agent such as borane in an ether. solvent (e.g. tetrahydrofuran) optionally in the presence of a suitable acid (e.g. trifluoroacetic acid, hydrochloric acid or the like), and heating the reaction mixture to reflux for about 3 to 5 hours. Alternatively, the reduction may employ catalytic hyrogenation in the presence of a noble metal catalyst, such as platinum, palladium or the like, in a suitable organic solvent, such as an alcoholic solvent, e.g. ethanol, conveniently at a temperature in the range of 0° to 100° C., aptly at room temperature.

Alternatively, compounds of formula (IIIa) and (IIIb) in which p=0,1

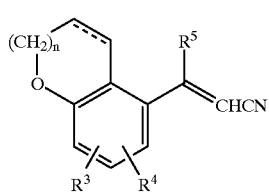
(IIIa)

may be converted to the compound of formula (II) in which $R^2$ is hydrogen and m is 2,3 or 4 by hydrogenation preferably in a suitable solvent such as acetic acid in the presence of for example, palladium on charcoal with platinum and/or rhodium on charcoal. This process is carried out at a pressure of 50–180 psi, peferably 50–110 psi and more preferably 70–100 psi a temperature in the range 30–100° C., preferably 30–80° C., more preferably 50° C. for a sufficient time period normally 24 hours.

Conveniently compounds (IIIb) may be converted directly into compounds (I) by carrying out this hydrogenation in the presence of an acid anhydride. The temperature and pressure may be adjusted to determine the degree of halogenation and unsaturation in the final product.

Compounds of formula (II) in which $R^2$ is $C_{1-6}$ alkyl may be prepared by N-alkylation of compounds of formula (II) in which $R^2$ is hydrogen using standard procedures.

Compounds of formula (III) may be-prepared from the following compounds of formula (IV)

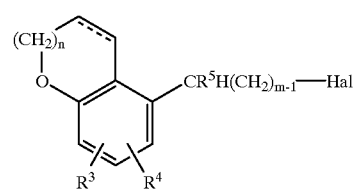
(IV)

wherein Hal represents one of the halide groups eg, chloride, bromide or iodide. The preparation involves reaction with an alkali metal cyanide such as potassium cyanide and the like, suitably in the presence of an alcoholic solvent. Compounds of formula (IIIa) and (IIIb) may be prepared from compounds of formula (V)

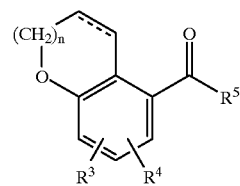
(V)

where $R^5$=H or $C_{1-6}$ alkyl. The preparation may conveniently be conducted using Wittig or Horner-Emmons type chemistry ie using a dialkyl cyanoalkyl phosphonate eg diethyl cyanomethyl phosphonate in the presence of a strong base eg sodium hydride in a suitable solvent eg THF.

In a particularly preferred embodiment of Route A Compounds of formula (II) where m is 2, n is zero, $R^5$ is H. and the dotted line does not represent a bond, (i.e. the 5 membered ring is saturated) may alternatively be prepared from compounds of formula (VI)

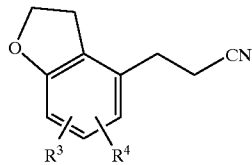
(VI)

by for example treatment heating under reflux with borane in tetrahydrofuran.

Compounds of formula (VI) may be prepared from a compound of formula (VII)

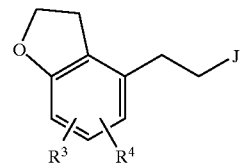
(VII)

wherein J represents a suitable leaving group, for example a mesylate group, a tosyl group or halogen by treatment with an organic cyanide, for example sodium cyanide.

Compounds of formula (VII) may be prepared from compounds of formula (VIII)

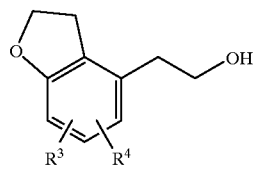
(VIII)

by reaction with suitable activating reagents, for example, methane sulfonyl chloride, tosyl chloride or a halogenating agent.

Compounds of formula (VIII) may be prepared from compounds of formula (IX).

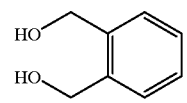
(IX)

by reaction with suitable acids, e.g. hydrochloride acid. If required, the substituents $R^3$ and/or $R^4$ (wherein $R^3$ and/or $R^4$ are both halogens) can be introduced into structure (VIII) with suitable reagents (e.g. N-bromosuccinimide if $R^3$ and/or $R^4$ is bromine or N-chlorosuccinimide if $R^3$ and/or $R^4$ is chlorine).

The compounds of formula (IX) may be prepared from the compound of formula (X)

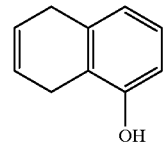
(X)

by ozonolysis. The compound of formula (X) is commercially available, or may be prepared by Birch reduction from the corresponding naphthol. At any stage in this process, compounds in which R3 and/or R4 are H or halogen may be modified into compounds in which R3 and/or R4 represent halogen, C1-6 alkyl or substituted aryl using reactions that would be apparent to a skilled person.

According to a further process (B), a compound of formula (I) where n=1 may be prepared by cyclisation of a compound of formula (XI)

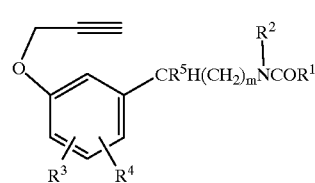
(XI)

The cyclisation is conveniently affected by heating in a suitable high boiling solvent (eg bromobenzene, N,N-diethylaniline). Compounds of formula (XI) may be prepared by alkylation of a compound of a compound of formula (XII)

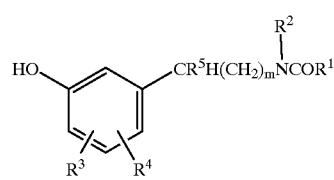
(XII)

using a propargyl halide (eg propargyl bromide) in the presence of a base such as potassium carbonate in a suitable solvent (eg DMF). Compounds of formula (XII) may be prepared by acylation of a compound of formula (XIII)

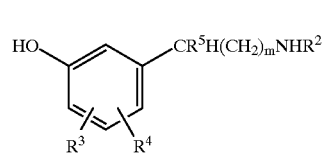
(XIII)

Suitable acylating agents and conditions which may conveniently be used in this process include those previously described for acylation of compounds of formula (II).

It will be appreciated that compounds of formulae (II), (III), (IV), (V), (VI), (VII), (VIII), (IX), (XI), (XII) and (XIII) and (XIV)–(XVIII) below are novel intermediates and represent further individual aspects of the present invention.

According to a further Process (C), the compounds of formula (I) in which $R^2$=H and in which m=2, 3, or 4 may be prepared from compounds of formula

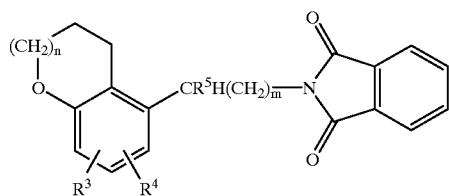
(XIV)

by treatment with a primary amine such as methylamine or hydrazine followed by acylation following the procedures described in Process (A).

Compounds of formula (XIV) may be prepared from alcohols of formula (XV)

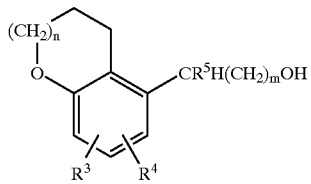
(XV)

by reaction with phthalimide under Mitsunobu conditions using for example triphenyl phosphine and diethyl azodicarboxylate in a suitable solvent such as tetrahydrofuran.

The alcohols of formula (XV) may be prepared by a number of methods apparent to the skilled person such as by reduction of acids or esters of formulae (XVI) or (XVII)

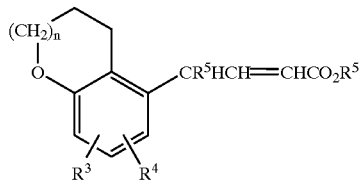
(XVI)

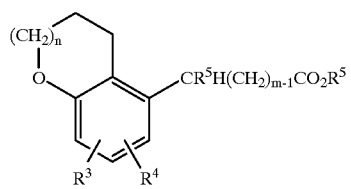
(XVII)

using for example lithium aluminium hydride in a suitable solvent such as tetrahydrofuran.

Such esters (XVI) and (XVII) are readily obtained using standard reactions. For example (XVI) may be prepared from aldehydes or ketones (V) via Wittig type reactions, or (XVII) may be made from halides (XVIII) using standard malonate type chemistry.

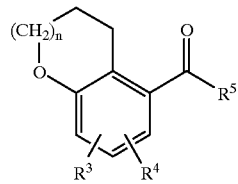
(V)

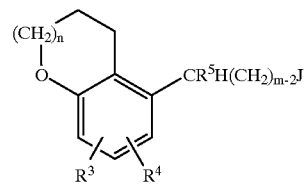
(XVIII)

There is further provided by the present invention a general interconversion process (D) wherein compounds of formula (I) can be converted into corresponding compounds of formula (I) by employing suitable reaction techniques. For example, compounds of formula (I) wherein $R^3$ represents a halogen atom, such as chlorine, may be converted into corresponding compound of formula (I) wherein $R^3$ represents hydrogen by appropriate reducing reactions. Compounds in which $R^3$ and/or $R^4$ represent hydrogen can be converted into compounds in which $R^3$ and/or $R^4$ represent a halogen by adding a suitable halogen compound to the compound in the presence of glacial acetic acid.

According to another general process (E), a compound of formula (I) may be prepared by subjecting a protected derivative of a compound of formula (I) to reaction to remove the protecting group or groups.

Thus, at an earlier stage in the preparation of a compound of formula (I) it may have been necessary and/or desirable to protect one or more sensitive groups in the molecule to prevent undesirable side reactions.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene (John Wiley and Sons 1991).

As will be appreciated, in general process (A) described above it may be desirable or even necessary to protect any sensitive groups in the molecule as just described. Thus, a reaction step involving deprotection of a protected derivative of general formula (I) or a salt thereof may be carried out subsequent to the above described process (A).

Compounds of the invention may be isolated in association with solvent molecules by crystaliisation from or evaporation of an appropriate solvent.

Individual enantiomers of the compounds of the invention may be prepared from racemates by resolution using methods known in the art for the separation of racemic mixtures into their constituent enantiomers, for example using chiral HPLC.

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The invention is further illustrated by the following Examples which should not be construed as constituting a limitation thereto.

Intermediate 1

4-Bromomethyl-7-chloro-benzofuran

A mixture of 7-chloro-4-methyl-benzofuran (CAS-number 79444-976; 51.9 g), N-bromosuccinimide (61.4 g), benzoyl peroxide (0.52 g) and carbon tetrachloride (1200 ml) was heated under reflux under the illumination of an 80 W flood lamp for 20 h. The mixture was cooled, and filtered and the filtrate evaporated to dryness. The residue was absorbed onto silica and purified by chromatography on silica using ethyl acetate and hexane (1:20) to give the title compound (39.50 g) as a yellow solid.

Tlc $SiO_2$(cyclohexane) Rf 0.30

Intermediate 2

7-Chloro-benzofuran-4-carbaldehyde

A solution of the N-methylmorpholine-N-oxide (37.64 g) in aoetonitrile (370 ml) containing 3 Å molecular sieves (36.6 g) was stirred at room temperature overnight and cooled in ice. A solution of 4-bromomethyl-7-chloro-benzofuran (39.44 g) in acetonitrile (90 ml) was added and the mixture stirred in at 0° C. for 4 h. The mixture was filtered and the filtrate evaporated to dryness. Water and ethyl acetate were added to the residue and the organic phase separated, dried ($Na_2SO_4$) and evaporated to give the title compound (21.3 g) as a pale yellow solid.

Tlc $SiO_2$(Ethyl acetate/cyclohexane 1:6) Rf 0.40

Intermediate 3

(E)-3-(7-Chloro-benzofuran-4-yl)-acrylonitrile and (Z)-3-(7-Chloro-benzofuran-4-yl)-acrylonitrile A solution of diethyl cyanomethylphosphonate (7.34 g) in dry tetrahydrofuran (20 ml) was added to a suspension of sodium hydride (60% oil dispersion; 1.65 g) in THF (40 ml) over 5 mins with ice cooling. After 15 min, a solution of 7-chloro-benzofuran-4-carbaldehyde in THF (20 ml) was added and after 5 mins the solution was warmed up and stirred at room temperature for 2 h. Brine (40 ml) and ethyl acetate (40 ml) were added, the phases separated and the aqueous extracted with ethyl acetate (2×20 ml). The extracts were dried ($MgSO_4$) and evaporated and the residue crystallised from ethanol to give off-white fluffy needles (2.95 g) of (E)-3-(7-Chloro-benzofuran-4-yl)-acrylonitrile.

Mass Spec Found $MNH_4^+$=221

The mother liquors were evaporated and the residue (6 g) chromatographed on silica using ethyl acetate:hexane (1:5 changing to 1:4) to give more of the E-isomer (1.19 g) and a sample of the Z-isomer (0.62 g). Mass Spec Found $MNH_4^+$=221

Tlc $SiO_2$ (Ethyl acetatelhexane 1:5) E-isomer Rf 0.55, Z-isomer Rf 0.35

Intermediate 4

3-(2,3-Dihydro-benzofuran-4-yl)-propylamine hydrochloride

A solution of the (E)-3-(7-chloro-benzofuran-4-yl)-acrylonitrile (intermediate 3) (1.0 g) in acetic acid (30 ml) containing 10% palladium on charcoal (50 mg; 50% wet paste) and 5% platinium on charcoal (50 mg) was hydrogenated at 100 psi and 50° for 3 days. The solution was filtered through hyflo and evaporated to dryness and the residue recrystallised from isopropanol to give the title compound as white plates (583 mg).

Tlc $SiO_2$ (Dichloromethane/methanol/0.880 ammonia 75:8:1) Rf 0.25

Mass spectrum $MH^+$ 178

Subjecting the Z-isomer to hydrogenation under similar conditions gave the same product.

Alternative Route

A solution of 2-(2,3-dihydrobenzofuran-4-yl)-propanonitrile (1.20 g) in tetrahydrofuran (12 ml) was treated with a 1M solution of borane in tetrahydrofuran (12 ml) and the solution was heated at reflux for 1 h. The solution was cooled to 20° and quenched with methanol (0.5 ml) followed by 5M hydrochloric acid (8 ml). The solution was heated at reflux for 30 min then cooled to 20° and basified with 10M sodium hydroxide (7 ml). The mixture was extracted with tert-butyl methyl ether (25 ml+12 ml). The combined extracts were dried ($K_2CO_3$) and the solvent evaporated to give the free base of the title compound (1.43 g) as a yellow oil.

Mass spectrum $MH^+$ 178.

Intermediate 5

3-(5-Bromo-2,3-dihydro-benzofuran-4-yl)-propylamine

A solution of the free base (200 mg) liberated from 3-(2,3-dihydro-benzofuran-4-yl)-propylamine hydrochloride and N-bromosuccinimide (215 mg) in acetic acid (5 ml) was stirred at room temperature overnight. The solution was evaporated to dryness and the residue taken up in water, basified to pH9–10 with 2N sodium hydroxide and extracted with ethyl acetate. The extracts were dried and evaporated to give the title compound (256 mg) as a pale yellow oil. Tic $SiO_2$ (Dichloromethane/methanol/0.880 ammonia 75:8:1) Rf 0.53

Mass spectrum found $MH^+$ 256/258

The hydrochloride salt was prepared by dissolving the title compound in methanolic HCl and evaporating the solvent to give a colourless solid.

Intermediate 6

2-(7-Chloro-benzofuran-4-ylmethyl)-malonic acid diethyl ester

Diethyl malonate (1.7 ml) was added dropwise to a suspension of sodium hydride (60%; 0.3 g) in dry THF (40 ml) at 0° under nitrogen. The mixture was allowed to warm to room temperature over 15 mins. Then a solution of 4-bromomethyl-7-chloro-benzofuran in dry THF (10 ml) was added in one portion and the mixture stirred for 1 h; then partitioned between water (100 ml) and ethyl acetate (3×50 ml). The combined organic extracts were washed with brine (50 ml), dried ($MgSO_4$) and evaporated to give the title compound as a pale yellow oil (2.466 g)

Tic $SiO_2$ (Ether/cyclohexane 1:5) Rf 0.33

Intermediate 7

3-(7-Chloro-benzofuran-4-yl)-acrylic acid methyl ester

Trimethylphosphonoacetate (363 mg) in dry DME (1 ml) was added dropwise to a suspension of sodium hydride (60%; 329 mg) in dry DME (20 ml) at 0° under nitrogen. The resulting white precipitate was stirred for 40 mins at room temperature, then a solution of 7-chloro-benzofuran-4-carbaldehyde (intermediate 2) (1.238 g) in dry DME (15 ml) was added at room temperature over 1 min. The mixture was heated under reflux for 2 h, cooled to room temperature, then partitioned between water (150 ml) and ether (100 ml). The. combined organic extracts were washed with brine (100 ml) and dried ($MgSO_4$). The solvent was evaporated to give the title compound as a colourless solid (1.59 g)

Tic $SiO_2$ (Dichloromethane/cyclohexane 1:1) Rf 0.35

Intermediate 8

3-(7-Chloro-benzofuran-4-yl)-propionic acid ethyl ester

A mixture of 2-(7-chloro-benzofuran-4-ylmethyl)-malonic acid diethyl ester (2.47 g) and sodium chloride (0.656 g) in DMSO (12 ml) and water (0.5 ml) was heated at 200° for 4 h under nitrogen. The cooled mixture was partitioned between water (80 ml) and ether (3×50 ml) and the combined organic extracts washed with brine (3×50 ml)

and dried (MgSO$_4$). The solvent was evaporated to give the title compound as a brown oil (1.28 g)

Tlc SiO$_2$ (Ether/cyclohexane 1:5) Rf 0.4

Intermediate 9

3-(7-Chloro-benzofuran-4-yl)-propan-1-ol

Route A

Lithium aluminium hydride (1.0M in ether; 0.24 ml) was added dropwise to a solution of 3-(7-chloro-benzofuran-4-yl)-acrylic acid methyl ester (intermediate 7) (0.1 g) in dry THF(5 ml) at 0° under nitrogen. The mixture was stirred at 0° for 5 mins, then water (0.2 ml) in THF (2 ml) added dropwise. The solvent was evaporated and the residue partitioned between hydrochloric acid (2N; 10 ml) and ether (3×20 ml). The combined organic extracts were washed with brine (20 ml) and dried (MgSO$_4$). The solvent was evaporated and the residue purified by column chromatography, eluting with ether/cyclohexane 2:1 gave the title compound as a colourless gum (29 mg)

Tlc SiO$_2$ (Ether/cyclohexane 2:1) Rf 0.25

Route B

Lithium aluminium hydride (1.0M in ether; 2.5 ml) was added dropwise to a solution of 3-(7-chloro-benzofuran-4-yl)-propionic acid ethyl ester (intermediate 8) (0.588 g) in dry THF(intermediate 8) (5 ml) at 0° under nitrogen. The mixture was allowed to warm to room temperature and stirred for 0.5 h, cooled to 0° and water (1 ml) in THF (5 ml) added dropwise. Hydrochloric acid (2N; 2 ml) was added followed by water (10 ml) and the mixture extracted with ethyl acetate (3×20 ml). The combined organic extracts were washed with brine (20 ml) and dried (MgSO$_4$). The solvent was evaporated and the residue purified by column chromatography, eluting with ether/cyclohexane 3:2 gave the title compound as a colourless gum (360 mg)

Tlc SiO$_2$ (Ether/cyclohexane 2:1) Rf 0.25

Intermediate 10

2-[3-(7-Chloro-benzofuran-4-yl)-propyl]-isoindole-1,3-dione

Diethylazodicarboxylate (0.35 ml) was added dropwise to a solution of triphenylphosphine (587 mg) and phthalimide (329 mg) in dry THF (10 ml) at 0° under nitrogen. A solution of 3-(7-chloro-benzofuran-4-yl)-propan-1-ol (364 mg) in THF (5 ml) was then added and the mixture allowed to warm to room temperature and stirred for 2 h. The solvent was evaporated and the residue purified by column chromatography, eluting with cyclohexane/ether 3:1 gave the title compound as a colourless solid (521 mg)

Tlc SiO$_2$ (Cyclohexane/ether 3:1) Rf 0.24

Intermediate 11

1-Chloro-4-(2,2-diethoxy-ethoxy)-2-methyl-benzene

A mixture of 4-chloro-3-methylphenol (47 g), bromoacetaldehyde diethyl acetal (45 ml) and potassium hydroxide (33.6 g) in dimethyl sulphoxide (250 ml) was heated at 120° for 2 h. The cooled mixture was partitioned between water (750 ml) and toluene (3×500 ml) and the combined organic extracts washed with brine/water 1:1 (3×300 ml) and dried (Na$_2$SO$_4$). The solvent was evaporated to give the title compound as a pale yellow oil (67.9 g)

Tlc SiO$_2$ (Hexane) Rf 0.2

Intermediate 12

5-Chloro-4-methyl-benzofuran mixture with 5-chloro-6-methyl-benzofuran

A solution of 1-chloro-4-(2,2-diethoxy-ethoxy)-2-methyl-benzene (36.2 g) in toluene (150 ml) was added dropwise to a solution of polyphosphoric acid (72 g) in toluene (200 ml) at 100° under nitrogen. The mixture was heated at 100° for 1 h, cooled to room temperature and sodium hydroxide (2M,400 ml) was added. The organic phase was separated and the aqueous extracted further with toluene (2×200 ml). The combined organic extracts were dried (Na$_2$SO$_4$) and evaporated. The residue was purified by column chromatography. Elution with cyclohexane gave the title compound as a pale yellow oil (20.1 g)

Tlc SiO$_2$ (Cyclohexane) Rf 0.54

Intermediate 13

4-Bromomethyl-5-chloro-benzofuran mixture with 6-bromomethyl-5-chloro-benzofuran A mixture of 5-chloro-4-methyl-benzofuran with 5-chloro-6-methyl-benzofuran (19.6 g), N-bromosuccinimide (23 g) and benzoyl peroxide (160 mg) in carbon tetrachloride (350 ml) was heated under reflux under a 200 W lamp for 36 h. The cooled mixture was filtered through hyflo and the filtrate evaporated to give the title compound as a dark oil (28.8 g)

Tlc SiO$_2$ (Cyclohexane) Rf 0.6

Intermediate 14

5-Chloro-benzofuran-4-carbaldehyde mixture with 5-chloro-benzofuran-6-carbaldehyde A solution of 4-bromomethyl-5-chloro-benzofuran mixture with 6-bromomethyl-5-chloro-benzofuran (30.54 g) in dry acetonitrile (80 ml) was added dropwise to a mixture of N-methylmorpholine-N-oxide (29.14 g) and 4 Å molecular sieves in dry acetonitrile (100 ml) at 100 under nitrogen. The mixture was stirred at room temperature for 5 h, filtered through hyflo and the filtrate evaporated. The residue was triturated under ether (100 ml) and filtered. The filtrate was evaporated and the residue recrystalised from cyciohexane to give the title compound as a pale yellow solid (10.95 g)

Tlc SiO$_2$ (Dichloromethane/Hexane 1:1) Rf 0.3

Intermediate 15

(E)-3-(5-Chloro-benzofuran-4-yl)-acrylonitrile mixture with (E)-3-(5-Chloro-benzofuran-6-yl)-acrylonitrile A solution of diethyl cyanomethylphosphonate (11.5 ml) in dry ethylene glycol dimethyl ether (DME; 10 ml) was added dropwise to a suspension of sodium hydride (60%; 2.914 g) in DME (50 ml) at 0° under nitrogen. The mixture was stirred at 0° for 20 mins. Then a solution of 5-chloro-benzofuran-4-carbaldehyde mixture with 5-chloro-benzofuran-6-carbaldehyde (10.95 g) in DME (50 ml) was added in one portion. The mixture was heated at 60° for 2 h, cooled to room temperature and partitioned between water (150 ml) and ether (3×100 ml). The combined organic extracts were washed with brine (2×100 ml) and dried (MgSO$_4$). The solvent was evaporated and the residue purified by column chromatography. Elution with cyclohexane/ethyl acetate 20:1 gave the title compound as a colourless solid (6.75 g)

Tlc SiO$_2$ (Cyclohexane/ethyl acetate 8:1) Rf 0.31

Intermediate 16

3-(5-Chloro-benzofuran-4-yl)-propylamine mixture with 3-(5-chloro-benzofuran-6-yl)-propylamine A solution of (E)-3-(5-chloro-benzofuran-4-yl)-acrylonitrile mixture with (E)-3-(5-chloro-benzofuran-6-yl)-acrylonitrile (intermediate 15) (1 g) in ethanolic ammonia (1.0M, 50 ml) was hydrogenated over rhodium on alumina (130 mg) for 18 h. The catalyst was filtered off and the filtrate evaporated. The residue was purified by column chromatography , eluting with dichloromethane/ethanol/ammonia 100:8:1 gave the title compound as a pale yellow gum (616 mg)

Tlc SiO$_2$ (Dichloromethane/ethanol/ammonia 100:8:1) Rf 0.15

Intermediate 17

2-(2,2-Dimethoxy-ethoxy)-1-fluoro-4-methyl-benzene

Bromoacetaldehyde dimethyl acetal (42 ml) was added to a mixture of 2-fluoro 5-methyl phenol[1] (22.05 g) and potassium hydroxide pellets (19.6 g) in dimethyl sulphoxide (160 ml) at room temp under nitrogen. The mixture was heated at 100° for 16 h, cooled to room temp and partitioned between water (500 ml) and ether (3×200 ml). The combined organic extracts were washed with brine/water 1:1, (3×200 ml) and dried (MgSO$_4$). The solvent was evaporated to give the title compound as an orange oil (48 g)

Reference 1: Singh S et al, J Amer. Chem Soc 1987, 109, (23), 7194–7196.

Tlc (Cyclohexane) Rf 0.4

Intermediate 18

7-Fluoro-4-methyl-benzofuran

A solution of 2-(2,2-dimethoxy-ethoxy)-1-fluoro-4-methyl-benzene (48 g) in toluene (50 ml) was added dropwise to a refluxing solution of polyphosphoric acid (100 g) in toluene (350 ml) under nitrogen. The mixture was heated under reflux for 3 h, cooled to room temperature and sodium hydroxide (2N; 800 ml) added. The mixture was extracted with ether (3×300 ml) and the combined organic extracts washed with brine (2×300 ml) and dried (MgSO$_4$). The solvent was evaporated and the residue purified by column chromatography. Eluting with hexane gave the title compound as a pale yellow oil (14.2 g)

Tlc SiO$_2$ (Hexane) Rf 0.4

Intermediate 19

4-Bromomethyl-7-fluoro-benzofuran

A mixture of 7-fluoro-4-methyl-benzofuran (14.2 g), N-bromosuccinimide (19.7 g), benzoyl peroxide (0.5 g) and carbon tetrachloride (600 ml) was heated under reflux under the illumination of an 80 W flood lamp for 20 h. The mixture was cooled, and filtered and the filtrate evaporated to dryness to give the title compound as a pale orange oil (23.4 g)

Tlc (cyclohexane) Rf 0.18

Intermediate 20

7-Fluoro-benzofuran-4-carbaldehyde

A solution of the N-methylmorpholine-N-oxide (22.24) in acetonitrile (250 ml) containing 3 Å molecular sieves (8.71 g) was stirred at room temperature overnight, then cooled in ice. A solution of 4-bromomethyl-7-fluoro-benzofuran (23.45 g) in acetonitrile (50 ml) was added and the mixture stirred for 4 h. The mixture was filtered and the filtrate evaporated to dryness. Water and ether were added to the residue and the organic phase separated, washed with brine (2×200 ml), dried (MgSO$_4$) and evaporated. The residue was triturated under ether (50 ml) and filtered to give the title compound as a pale yellow solid (5.45 g)

Tlc SiO$_2$ (Dichloromethane/hexane 1:1) Rf 0.30

Intermediate 21

(E)-3-(7-Fluoro-benzofuran-4-yl)-acrylonitrile

A solution of diethyl cyanomethylphosphonate (5.35 g) in dry ethylene glycol dimethyl ether (DME; 20 ml) was added to a suspension of sodium hydride (60% oil dispersion; 1.32 g) in DME (20 ml) at 0° under nitrogen over 5 mins. After 15 min, a solution 7-fluoro-benzofuran-4-carbaldehyde (4.51 g) in DME (20 ml) was added and after 5 mins the solution was warmed up and stirred at room temperature for 2 h. Ammonium chloride solution (200 ml) and ethyl acetate (150 ml) were added, the phases separated and the aqueous extracted with ethyl acetate (2×150 ml). The extracts were dried (MgSO$_4$) and evaporated and the residue triturated under ether (20 ml) and filtered to give the E isomer as a buff coloured solid (3.07 g)

The mother liquors were evaporated to give a mixture of E and Z isomers (4.25 g)

Tlc SiO$_2$ (Hexane/Dichloromethane 1:1) Rf 0.40

Intermediate 22

3-(7-Fluoro-2,3-dihydro-benzofuran-4-yl)-propylamine

A solution of (E)-3-(7-fluoro-benzofuran-4-yl)-acrylonitrile (0.25 g) in ethanol (25 ml), ammonia (0.88; 10 ml) containing 10% palladium on charcoal (50 mg; 50% wet paste) and 5% rhodium on charcoal (50 mg) was hydrogenated at 70 psi and 70° for 18 h. The solution was filtered through hyflo and evaporated to dryness and the residue purified by column chromatography. Eluting with dichloromethane/ethanol/ammonia 100:8:1 gave the title compound (256 mg).

Tlc (Dichloromethane/methanol/0.880 ammonia 100:8:1) Rf 0.20; Mass spectrum Found MH$^+$ 196

Intermediate 23

3-(5-chloro-2,3-dihydro-benzofuran-4-yl)propylamine hydrochloride

A solution of of 3-(2,3-dihydro-benzofuran-4-yl)-propylamine hydrochloride (150 mg) and N-chlorosuccinimide (100 mg) in acetic acid (50 ml) was stirred at room temperature overnight. The solution was evaporated to dryness and the residue taken up in water, basified with 2N sodium hydroxide and extracted with dichloromethane. The extracts were dried and evaporated and the residue disolved in a solution of hydrogen chloride in methanol. Evaporation gave the the title compound (159 mg) as an off-white powder after trituration with ether.

Mass spectrum Found MH$^+$ 212/214.

Intermediate 24

Cyclopropanecarboxylic acid [3-(3-hydroxy-phenyl)-propyl]-amide

Cyclopropanecarbonyl chloride (0.063 ml) was added dropwise to a suspension of 3-(3-amino-propyl)-phenol[1] (0.1 g) and N,N-diisopropylamine (0.23 ml) in dichloromethane (15 ml) in an ice bath under nitrogen. The mixture was then stirred for 3 h at room temperature, then purified by passing through a solid phase extraction cartridge. Elution with chloroform followed by ethyl acetate gave the title compound as a colourless gum (122 mg)

1. T.Kametani et al J. Chem. Soc. Perkin Trans 1, 1974, 22, 2602–2604

TLC SiO$_2$ (Ether) Rf 0.34

Intermediate 25

Cyclopropanecarboxylic acid [3-(3-prop-2-ynyloxy-phenyl)-propyl]-amide

Propargyl bromide (80% in toluene, 0.091 ml) was added dropwise to a mixture of cyclopropanecarboxylic acid [3-(3-hydroxy-phenyl)-propyl]-amide (122 mg) and potassium carbonate (154 mg) in dry DMF (10 ml) in an ice bath under nitrogen. The mixture was allowed to warm to room temperature, then heated at 65° C. for 18 h. The cooled mixture was partitioned between water (50 ml) and ethyl acetate (3×15 ml). The combined organic extracts were washed with brine/water 1:1 (3×20 ml) and dried (MgSO$_4$). The solvent was evaporated and the residue purified by column chromatography on silica. Elution with hexane/ethyl acetate 2:1 gave the title compound as a colourless solid (79 mg)

Tlc SiO$_2$ (Hexane/ethyl acetate 2:1) Rf 0.18

Intermediate 26

1-(2,2-Dimethoxyethoxy)-4-fluoro-3-methylbenzene

A mixture of 4-fluoro-3-methylphenol (36.7 g), potassium hydroxide pellets (19.5 g) and bromoacetaldehyde dimethyl acetal (34.6 ml) in dimethyl sulphoxide (240 ml) was heated at 110° for 24 h. The mixture was cooled, diluted with water (350 ml) and extracted with hexane. Evaporation of the extracts gave the title compound as an oil (52.3 g).

Mass spec. Found MNH$_4^+$ 232

Intermediate 27

5-Fluoro-4-methylbenzofuran mixture with 5-Fluoro-6-methylbenzofuran

Polyphosphoric acid (185 g) was heated to 100° and a solution of 1-(2,2-dimethoxyethoxy)-4-fluoro-3-methylbenzene (52.3 g) in toluene (520 ml) added. The mixture was stirred under reflux for 5 h, cooled and the toluene decanted off. The solution was concentrated and the residue passed through silica (900 g) eluting with hexane. Evaporation gave the title compound as a colourless liquid (14.95 g).

Tlc (hexane) Rf 0.60

Intermediate 28

4-Bromomethyl-5-fluorobenzofuran mixture with 6-Bromomethyl-5-fluorobenzofuran

A mixture of 5-fluoro-4-methylbenzofuran and 5-fluoro-6-methylbenzofuran (14.95 g), N-bromosuccinimide (16.57 g), benzoyl peroxide (0.32 g) and carbon tetrachloride (375 ml) was heated under reflux under the illumination of an 80 W flood lamp for 20 h. The mixture was cooled, and filtered and the filtrate evaporated to dryness to give the crude product as an oil (24.0 g). This material was combined with a similar crude product (6.94 g) from an identical reaction run on a smaller scale and purified by chromatography on silica (900 g) using an ether hexane mixture (1:30) as eluant to give the title compound (13.5 g) as an oil.

Tlc (hexane) Rf 0.38

Intermediate 29

5-Fluorobenzofuran-4-carbaldehyde (A) mixture with 5-Fluorobenzofuran-6-carbaldehyde (B)

A solution of the N-methylmorpholine-N-oxide (13.6 g) in acetonitrile (135 ml) containing 3 Å molecular sieves (13.2 g) was stirred at room temperature overnight and cooled in ice. A solution of 4-bromomethyl-5-fluorobenzofuran and 6-bromomethyl-5-fluorobenzofuran (13.33 g) in acetonitrile (35 ml) was added and the mixture stirred at 5° for 4 h. The mixture was filtered and the filtrate evaporated to dryness. Water and ethyl acetate were added to the residue and the organic phase separated, dried and evaporated to give the mixture of aldehydes. The mixture was separated by chromatography on silica (600 g) using a mixture of ethyl acetate and hexane (1:9) as the eluant to give the title compound (A) (2.19 g);

Tlc (Ethyl acetate/hexane 1:9) Rf 0.47; Mass spec. Found $MNH_4^+$ 182; and the title compound (B) (2.17 g); Tlc (Ethyl acetate/hexane 1:9) Rf 0.35; Mass spec. Found $MNH_4^+$ 182

Intermediate 30

(E)-3-[5-Fluororobenzofuran-4-yl]acrylonitrile and (Z)-3-[5-Fluorobenzofuran-4-yl]acrylonitrile.

A solution of diethyl cyanophosphonate (2.79 g) in dry tetrahydrofuran (10 ml) was added to a suspension of sodium hydride (60% oil dispersion; 0.63 g) in THF (16 ml) over 5 mins with ice cooling. After 15 min, a solution of 5-fluorobenzofuran-4-carbaldehyde (2.15 g) in THF (10 ml) was added and after 5 mins the solution was warmed up and stirred at room temperature for 3 h. Brine (20 ml) and ethyl acetate (20 ml) were added, the phases separated and the aqueous extracted with ethyl acetate (2×25 ml). The extracts were dried and evaporated and the residue purified by chromatography (Biotage Flash 40; 90 g; ethyl acetate:hexane 1:9) to give the title compound as a cream solid (1.97 g)

Tlc (Ethyl acetate/hexane 1:9) Rf 0.25; Mass spectrum $MNH_4^+$ 205

Intermediate 31

3-(2,3-Dihydro-5-fluorobenzofuran-4-yl)propylamine hydrochloride

N-[3-[2,3-Dihydro-5-fluorobenzofuran-4-yl]propyl] acetamide (0.55 g) was heated under reflux in 2M hydrochloric acid (10 ml) for 24 h. The mixture was cooled and washed with dichloromethane, basified with 2M sodium hydroxide and extracted with dichloromethane. Evaporation of the extracts gave an oil which was dissolved in 0.7M methanolic hydrogen chloride (8 ml). Evaporation gave the title compound as a beige solid (0.28 g).

Mass spectrum $MH^+$ 196

Intermediate 32

2,3-Bis(2-hydroxyethyl)-phenol

A solution of 5,8-dihydronaphth-1-ol (2.00 g) in methanol (40 ml) was cooled to −70° and ozone in oxygen was bubbled through the solution until tlc indicated that all the starting material had been consumed. The ozone was switched off and nitrogen bubbled through the solution for 5 min. Sodium borohydride (454 mg) was then added and the solution allowed to warm slowly to 20°. A further portion of sodium borohydride (227 mg) was added, followed 10 min later, by acetic acid (1 ml) and then the solvent was evaporated. The residue was partitioned between 2M hydrochloric acid (50 ml) and ethyl acetate (2×50 ml). The combined ethyl acetate extracts were dried ($Na_2SO_4$) and the solvent evaporated to give a brown oil which was purified by chromatography on silica gel eluting with ethyl acetate to give the title compound (1.49 g) as a pale brown oil which crystallised on prolonged standing.

Tlc $SiO_2$ (ethyl acetate) Rf 0.46.

Intermediate 33

2-(2,3-Dihydrobenzofuran-4-yl)-ethanol

A mixture of 2,3-bis(2-hydroxyethyl)-phenol (1.2 g) and 36% aqueous hydrochloric acid (24 ml) was heated at reflux for 2 h. The mixture was cooled, diluted with water (24 ml) and extracted with ethyl acetate (2×24 ml). The combined extracts were dried ($Na_2SO_4$) and the solvent evaporated to give the title compound (1.2 g) as a brown oil.

Tlc $SiO_2$ (ethyl acetate) Rf 0.67.

Intermediate 34

Methanesulfonic acid 2-(2,3-dihydrobenzofuran-4-yl)-ethyl ester

A solution of 2-(2,3-dihydrobenzofuran-4-yl)-ethanol (1.13 g) in dichloromethane (11 ml) was treated with triethylamine (1.25 ml), followed by methanesulfonyl chloride (0.64 ml). After 5 min the reaction mixture was poured into 2M hydrochloric acid (10 ml) and extracted with dichloromethane (2×10 ml). The combined extracts were washed with water (10 ml), dried ($Na_2SO_4$) and the solvent evaporated to give the title compound (1.76 g) as a yellow oil.

Tlc $SiO_2$ (iso-hexane/ethyl acetate 1:1) Rf 0.43.

Intermediate 35

3-(2,3-Dihydrobenzofuran-4-yl)-propanonitrile

A solution of methanesulfonic acid 2-(2,3-dihydrobenzofuran-4-yl)-ethyl ester (1.71 g) in dimethylsulfoxide (14 ml) was treated with sodium cyanide (381 mg) and heated at 80° for 1 h. The suspension was cooled to 20°, diluted with water (14 ml) and extracted with ethyl acetate (2×17 ml). The combined extracts were washed with 5% aqueous sodium chloride (17 ml), dried ($Na_2SO_4$) and the solvent evaporated to give the title compound (1.22 g) as a brown oil which crystallised on standing.

Tlc $SiO_2$ (iso-hexane/ethyl acetate 1:1) Rf 0.62.

EXAMPLE 1

N-[3-(5-Bromo-2,3-dihydro-benzofuran-4-yl)-propyl]-acetamide

A solution of 3-(5-bromo-2,3-dihydro-benzofuran-4-yl)-propylamine (256 mg) in pyridine (3 ml) at 40 was treated with acetic anhydride (0.11 ml) and the solution stored overnight at 4°. The cold solution was acidified with 2N hydrochloric acid and the mixture extracted with ethyl acetate. The extracts were dried and evaporated and the residue chromatographed on silica (20 g) using dichloromethane:methanol:ammonia (100:8:1) to give the title compound as an oil which slowly solidified (175 mg).

Tlc SiO$_2$ (Dichloromethane/methanol/0.880 ammonia 75:8:1) Rf 0.67; Mass spectrum MH$^+$ Found 297/299

EXAMPLE 2
N-[3-(7-Chloro-benzofuran-4-yl)-propyl]-acetamide

A solution of 2-[3-(7-chloro-benzofuran-4-yl)-propyl]-isoindole-1,3-dione (0.5 g) in ethanolic methylamine (10 ml) was stirred at room temperature for 4 h. The solvent was evaporated and the residue suspended in dry THF (15 ml) and cooled to 0° C. Pyridine (0.27 ml) and acetic anhydride (0.2 ml) were added and the mixture allowed to warm to room temperature and stirred for 18 h. The solvent was evaporated and the residue purified by column chromatography, eluting with dichloromethane/methanol 100:1 gave the title compound as a colourless solid (230 mg) mp 61–62°

Tlc SiO$_2$ (Dichloromethane/methanol 50:1) Rf 0.16

A solution of E- and Z-3-[7-chlorobenzofuran-4-yl]acrylonitrile (4.0 g) in acetic acid (100 ml) and acetic anhydride (3.7 ml) containing 10% palladium on charcoal (200 mg; 50% wet paste) and 5% platinium on charcoal (200 mg) was hydrogenated at 100 psi and 60° for 24 h. An aliquot (10 ml) was removed and methanol (1 ml) added to it. After 16 h the solution was filtered and evaporated and the residue purified by chromatography (Biotage Flash 40; ethyl acetate) to give the title amide (99 mg) as an oil.

Tlc (Ethyl acetate) Rf 0.30; Mass spectrum MH$^+$ 252/254

EXAMPLE 3
N-[3-(7-Chloro-2,3-dihydro-benzofuran-4-yl)-propyl]-acetamide

A solution of N-[3-(7-chloro-benzofuran-4-yl)-propyl]-acetamide (48 mg) in ethanol (15 ml) was hydrogenated over rhodium catalyst (5% on carbon; 15 mg) over 7 h. The catalyst was filtered off and the filtrate evaporated. The residue was purified by column chromatography, eluting with dichloromethane/methanol 50:1 gave the title compound as a colourless solid (37.6 mg) mp 76–78°

Mass Spec Found MH$^+$ 254/256; Tlc SiO$_2$ (Dichloromethane/methanol 50:1) Rf 0.16

EXAMPLE 4
N-[3-(2,3-Dihydro-benzofuran-4-yl)-propyl]-acetamide

A solution of the N-[3-(7-chloro-2,3-dihydro-benzofuran-4-yl)-propyl]-acetamide, (78 mg) in ethanol (5 ml) was hydrogenated over palladium (10%; 20 mg) over 64 h. The catalyst was filtered off and the filtrate concentrated in vacuo. The residue was purified by column chromatography, eluting with dichloromethane/methanol 50:1 gave the title compound as a colourless solid (54 mg) mp 66–67° C.

Assay Found: C, 71.0; H, 8.1; N, 6.6; C$_{13}$H$_{17}$NO$_2$ Requires: C, 71.2; H, 7.8; N, 6.4%; Tlc SiO$_2$ (Dichloromethane/Methanol 50:1) Rf 0.16

Alternative Route

A solution of E- and Z-3-[7-chlorobenzofuran-4-yl]acrylonitrile (15 g) in acetic acid (330 ml), acetic anhydride (19.6 ml) and triethylamine (30.75 ml) containing 10% palladium on charcoal (0.75g; 50% wet paste) and 5% platinium on charcoal (0.75 g) was hydrogenated at 150 psi and 75° for 4 days. More catalysts (as before) were added and the reaction continued for a further 24 h. The solution was filtered and evaporated and the residue partitioned between dichloromethane (250 ml) and water (150 ml). The organic layer was washed successively with water (150 ml), 2M hydrochloric acid (2×100 ml), water (100 ml) and 2M sodium carbonate (100 ml) and then dried and evaporated to give the title compound as an off-white solid (15.4 g).

Tlc (Dichloromethane/methanol 50:1) Rf 0.16; Mass spectrum MH$^+$ 220

EXAMPLE 5
N-[3-(5-Chloro-benzofuran-4-yl)-propyl]-acetamide

Acetic anhydride (1.95 ml) was added dropwise to a solution of 3-(5-chloro-benzofuran-4-yl)-propylamine mixture with 3-(5-chloro-benzofuran-6-yl)-propylamine (2.86 g) and pyridine (2.2 ml) in dry THF (70 ml) at 0° under nitrogen. The mixture was stirred at room temperature for 3 h, then evaporated to dryness in vacuo . The residue was purified by HPLC (CN-PK5-10530 column). Eluting with 5% isopropanol/heptane gave the title compound as a colourless solid (1.37 g) mp 82–83° C.

Tlc SiO$_2$ (Dichloromethane/ethanol/0.880 ammonia 100:8:1) Rf 0.39

EXAMPLE 6
N-[3-(5-Chloro-2,3-dihydro-benzofuran-4-yl)-propyl]-acetamide

A solution of N-[3-(5-chloro-benzofuran-4-yl)-propyl]-acetamide (0.25 g) in ethanol (15 ml) was hydrogenated over 5% rhodium on carbon (80 mg) for 18 h. The catalyst was filtered off and the filtrate evaporated. The residue was purified by column chromatography on silica, eluting with dichloromethane/methanol 40:1 gave the title compound as a colourless solid (131 mg) mp 91–92

Mass Spec Found MH$^+$=254.094828; C$_{13}$H$_{17}$ClNO$_2$ Requires 254.094782; Tlc SiO$_2$ (Dichloromethane/Methanol 50:1) Rf 0.22

EXAMPLE 7
N-[3-(5,7-Dichloro-2,3-dihydro-benzofuran-4-yl)-propyl]-acetamide

N-Chlorosuccinimide (173 mg) was added to a solution of N-[3-(5-chloro-2,3-dihydro-benzofuran-4-yl)-propyl]-acetamide (0.2 g) in glacial acetic acid (5 ml) at room temperature under nitrogen and the mixture stirred for 64 h. The solution was adusted to pH 9 with sodium carbonate (2N; 10 ml) and extracted with ethyl acetate (3×15 ml). The combined organic extracts were washed with brine (20 ml) and dried (MgSO$_4$). The solvent was evaporated and the residue purified by HPLC, eluting with 50% acetonitrile/water+0.1% TFA gave the title compound as a colourless gum (97 mg)

Mass Spec Found MH$^+$=288.055872; C$_{13}$H$_{16}$Cl$_2$NO$_2$ requires 288.055809; Tlc SiO$_2$ (Dichloromethane/Methanol 50:1) Rf 0.22

EXAMPLE 8
N-[3-(7-Fluoro-2,3-dihydro-benzofuran-4-yl)-propyl]-acetamide

Acetic anhydride (0.18 ml) was added dropwise to a solution of 3-(7-fluoro-2,3-dihydro-benzofuran-4-yl)-propylamine (256 mg) in, dry THF (10 ml) containing pyridine (0.21 ml) at 0° under nitrogen and the solution stirred overnight at room temperature. The solution was evaporated and the residue purified by column chromatography. Eluting with dichloromethane:methanol: (50:1) gave the title compound as a colouriess oil (133 mg)

Tlc (Dichloromethane/methanol 50:1) Rf 0.18; Mass Spectrum Found MH+238, MNH$_4^+$ 255

EXAMPLE 9
N-[3-(5-Chloro-7-fluoro-2,3-dihydro-benzofuran-4-yl)-propyl]-acetamide N-Chlorosuccinimide (47.7 mg) was added to a solution of N-[3-(7-fluoro-2,3-dihydro-benzofuran-4-yl)-propyl]-acetamide (77 mg) in glacial acetic acid (5 ml) at room temperature under nitrogen and the mixture stirred for 72 h. The solution was evaporated and the residue partitioned between sodium carbonate (2N; 10 ml) and ethyl acetate (10 ml). The combined organic extracts were washed with brine (10 ml) and dried (MgSO$_4$). The solvent was evaporated and the residue purified by column chromatography. Eluting with dichloromethane/methanol 50:1 gave the title compound as a colourless gum which crystallised on standing (67 mg).

Mass Spec Found MH$^+$=272/274; Tlc SiO$_2$ (Dichloromethane/Methanol 50:1) Rf 0.18

EXAMPLE 10
N-[3-(5-Bromo-7-fluoro-2,3-dihydro-benzofuran-4-yl)-propyl]-acetamide N-Bromosuccinimide (569 mg) was added to a solution of N-[3-(7-fluoro-2,3-dihydro-benzofuran-4-yl)-propyl]-acetamide (690 mg) in glacial acetic acid (15 ml) at room temperature under nitrogen and the mixture stirred for 48 h. The solution was evaporated and the residue partitioned between sodium carbonate (2N; 20 ml) and ethyl acetate (20 ml). The combined organic extracts were washed with brine (25 ml) and dried (MgSO$_4$). The solvent was evaporated and the residue purified by column chromatography. Eluting with dichloromethane/methanol 50:1 gave the title compound as a colourlss solid (644 mg)

Mass Spec Found MH$^+$=316/318; Tlc SiO$_2$ (Dichloromethane/Methanol 50:1) Rf 0.18

EXAMPLE 11
Cyclopropanecarboxylic acid [3-(2,3-dihydro-benzofuran-4-yl)-propyl]-amide 3-(2,3-dihydro-benzofuran-4-yl)-propylamine hydrochloride (200 mg) was partitioned between 2N sodium hydroxide (10 ml) and dichloromethane (10 ml) and the organic phase separated, dried (Na$_2$SO$_4$) and evaporated. The residual free base (160 mg) and triethylamine (110 mg) were dissolved in dichloromethane (2 ml), cooled in ice and cyclopropane carbonyl chloride (103 mg) added. After 2 hours the solution was warmed up to room temperature and 2N hydrochloric acid (10 ml) added. The mixture was extracted with dichloromethane (3×20 ml), and the extracts washed with 8% sodium bicarbonate, dried (Na$_2$SO$_4$) and evaporated. The residue was purified by chromatography on silica using a mixture of ethyl acetate and hexane (1:1) as the eluant to give the title compound as a white solid (95 mg)

Mass Spec Found MH$^+$ 246; Tlc SiO$_2$ (Ethyl acetate/hexane 1:1) Rf 0.26

EXAMPLE 12
Cyclopropane carboxylic acid [3-(5-chloro-2,3-dihydro-benzofuran-4-yl)propyl]-amide A mixture of 3-(5-chloro-2,3-dihydro-benzofuran-4-yl)-propylamine hydrochloride (142 mg), dimethylformamide (5 drops), triethylamine (0.64 ml) and dichloromethane (5 ml) was stirred in ice for 20 minutes. Cyclopropanecarbonyl chloride (66 mg) was added and stirring continued for 5 hours. The mixture was purified by chromatography on silica eluting with ethyl acetate/hexane (1:1) to give the title compound as a white solid (80 mg).

Tlc (Ethyl acetate/Hexane 1:1) Rf 0.17; Mass spectrum Found MH+ 280/282

EXAMPLE 13
Cyclopropanecarboxylic acid [3-(5-bromo-2,3-dihydro-benzofuran-4-yl)propyl]-amide A mixture of 3-(5-bromo-2,3-dihydro-benzofuran-4-yl)-propylamine hydrochloride (100 mg), dimethylformamide (3 drops), triethylamine (0.35 ml) and dichloromethane (3 ml) was stirred in ice for 15 minutes. Cyclopropanecarbonyl chloride (36 mg) was added and stirring continued for 2 hours. The mixture was purified by chromatography on silica to give the title compound as a white solid (86 mg).

Tlc (Ethyl acetate:hexane 1:1) Rf 0.33; Mass spectrum Found MH+ 324/326

EXAMPLE 14
Cyclopropanecarboxylic acid [3-(7-fluoro-2,3-dihydro-benzofuran-4-yl)propyl]amide A mixture of 3-(7-fluoro-2,3-dihydro-benzofuran-4-yl)-propylamine (114 mg), triethylamine (0.089 ml), dichloromethane (5 ml) and cyclopropanecarbonyl chloride (67 mg) was stirred in ice for 20 minutes and stirring continued at room temperature overnight. The mixture was partitioned between 2N hydrochloric acid and dichloromethane and the organic phase washed with 8% sodium bicarbonate and evaporated. Purification of the residue by preparative hplc gave the title compound as a white solid (16 mg).

Tlc (Ethyl acetate/Hexane 1:1) Rf 0.12; Mass spectrum Found MH+ 264

EXAMPLE 15
Cyclopropanecarboxylic acid [3-(5-chloro-7-fluoro-2,3-dihydro-benzofuran-4-yl)-propyl]-amide A mixture of cyclopropanecarboxylic acid [3-(7-fluoro-2,3-dihydro-benzofuran-4-yl)-propyl]-amide (445 mg) and N-chlorosuccnimide (248 mg) in glacial acetic acid (15 ml) was stirred at room temperature for 72 h. The solvent was evaporated and the residual solid triturated under water (10 ml) and filtered to give the title compound as a colourless solid (236 mg).

Mass spec. Found MH$^+$ 298.1/300.1; Tlc SiO$_2$ (Hexane/ethyl acetate 1:1) Rf 0.18

EXAMPLE 16
Cyclopropanecarboxylic acid [3-(5-chloro-7-fluoro-benzofuran-4-yl)-propyl]-amide Lead tetraacetate (313 mg) was added to a solution of cyclopropanecarboxylic acid [3-(5-chloro-7-fluoro-2,3-dihydro-benzofuran-4-yl)-propyl]-amide (0.2 g) in glacial acetic acid (5 ml) and the mixture stirred at room temperature for 18 h. The solvent was evaporated and the resdue purified by preparitive HPLC to give the title compound as a colourless solid (20 mg).

Mass spec Found MH$^+$ 296.1/298.1; Tlc SiO$_2$ (Hexane/ethyl acetate 1:1) Rf 0.18

EXAMPLE 17
N-[3-(benzofuran-4-yl)-propyl]-acetamide

Lead tetraacetate (210 mg) was added to a solution of N-[3-(2,3-dihydro-benzofuran-4-yl)-propyl]-acetamide (100 mg) in acetic acid (1.5 ml) at 100. The mixture was stirred at room temperature for 2h and at 50° for 16 h. The solvent was evaporated and the residue purified by chromatography to give the title compound as an oil (41 mg).

Mass spec Found MH$^+$ 218; Tlc SiO$_2$ (ethyl acetate/hexane 2:1) Rf 0.43

EXAMPLE 18
Cyclopropanecarboxylic acid [3-(benzofuran-4-yl)-propyl]-amide

Lead tetraacetate (194 mg) was added to a solution of cyclopropanecarboxylic acid [3-(2,3-dihydro-benzofuran-4-yl)-propyl]-amide (100 mg) in acetic acid (1.5 ml) at 10°. The mixture was stirred at room temperature for 4 h and at 50° for 24 h. The solvent was evaporated and the residue purified by chromatography on silica. Elution with hexane/ethyl acetate gave the title compound as an oil (15 mg).

Mass spec Found MH+ 244; Tlc SiO₂ (Ethyl acetate/hexane 1:1) Rf 0.13

EXAMPLE 19
Cyclobutanecarboxylic acid [3-(2,3-dihydro-benzofuran-4-yl)-propyl]-amide 3-(2,3-Dihydro-benzofuran-4-yl)-propylamine hydrochloride (100 mg) was suspended in dichloromethane (3 ml) containing triethylamine (0.33 ml) and cooled in ice. A solution of cyclobutanecarbonyl chloride (0.054 ml) in dichloromethane (1 ml) was added and the mixture stirred in ice for 3 h. The mixture was purified by elution through a solid phase extraction cartridge to give the title compound as a white solid (110 mg).

Tlc SiO₂ (Ethyl acetate/hexane 1:1) Rf 0.33; Mass spectrum MH+ 260

EXAMPLE 20
Cyclopentanecarboxylic acid [3-(2,3-dihydro-benzofuran-4-yl)-propyl]-amide The compound was prepared by the method described in Example 19 using cyclopentanecarbonyl chloride (0.058 ml) to give the title compound as a white solid (90 mg).

Tlc SiO₂ (Ethyl acetate/hexane 1:1) Rf 0.43; Mass spectrum MH+ 274

EXAMPLE 21
2-Methylpropionic acid [3-(2,3-dihydro-benzofuran-4-yl)-propyl]-amide The compound was prepared by the method described in Example 19 using 2-methy-propionyl chloride (0.05 ml) to give the title compound as a white solid (93 mg).

Tlc SiO₂ (Ethyl acetate/hexane 1:1) Rf 0.35; Mass spectrum MH+ 248

EXAMPLE 22
Propionic acid [3-(2,3-dihydro-benzofuran-4-yl)-propyl]-amide

The compound was prepared by the method described in Example 19 using propionyl chloride (0.044 ml) to give the title compound as a white solid (71 mg).

Tlc SiO₂ (Ethyl acetate/hexane 1:1) Rf 0.22; Mass spectrum MH+ 234

EXAMPLE 23
Butyric acid [3-(2,3-dihydro-benzofuran-4-yl)-propyl]-amide

The compound was prepared by the method described in Example 19 using mebutyryl chloride (0.05 ml) to give the title compound as a white solid (67 mg).

Tlc SiO₂ (Ethyl acetate/hexane 1:1) Rf 0.27; Mass spectrum MH+ 248

EXAMPLE 24
Cyclopropanecarboxylic acid [3-(2H-chromen-7-yl)-propyl]-amide (A) and Cyclopropanecarboxylic acid [3-(2H-chromen-5-yl)-propyl]-amide (B)

A solution of cyclopropanecarboxylic acid [3-(3-prop-2-ynyloxy-phenyl)-propyl]-amide (415 mg) in N,N-diethylaniline (2 ml) was heated at 215° C. for 24 h. The cooled mixture was purified by column chromatography on silica. Elution with hexane/ethyl acetate 3:1 gave the title compound (A) as a colourless solid (16 mg)

Mass spec Found MH+ 258; Tlc SiO₂ (Hexane/ethyl acetate 2:1) Rf 0.27; and the title compound (B) as a colourless oil (79 mg); Mass spec Found MH+ 258; Tlc SiO₂ (Hexane/ethyl acetate 2:1) Rf 0.23

EXAMPLE 25
Cyclopropanecarboxylic acid (3-chroman-5-yl-propyl)-amide

A solution of cyclopropanecarboxylic acid [3-(2H-chromen-5-yl)-propyl]-amide (76 mg) in ethanol (5 ml) was hydrogenated over platinum (5% on carbon, 10 mg) for 16 h. The catalyst was filtered off and the filtrate evaporated. The residue was purified by column chromatography on silica. Elution with hexane/ethyl acetate 2:1 gave the title compound as a colourless solid (56 mg)

Mass spec Found MH+ 260.2; TLC SiO₂ (Hexane/ethyl acetate 2:1) Rf 0.23

EXAMPLE 26
N-[3-[2,3-Dihydro-5-fluorobenzofuran-4-yl]propyl]acetamide

A solution of the E- and Z-3-[5-fluororobenzofuran-4-yl] acrylonitriles (0.5 g) in acetic acid (20 ml) and acetic anhydride (1.25 ml) containing 10% palladium on charcoal (50 mg; 50% wet paste) and 5% platinium on charcoal (50 mg) was hydrogenated at 150 psi and 75° for 3 days. The solution was filtered through hyflo and evaporated to dryness and the residue purified by chromatography (Biotage Flash 40; 90 g; ethyl acetate:hexane 1:1 then changing to ethyl acetate) to give an impure sample of the title compound contaminated with N-[3-[4-fluorobenzofuran-4-yl] propyl]acetamide. This material was combined with a similar product obtained from an identical reaction and subjected to further hydrogenation in acetic acid (25 ml) containing 10% palladium on charcoal (50 mg; 50% wet paste) and 5% platinium on charcoal (50 mg) at 170 psi and 75° for 24 h. The solution was filtered and evaporated and the residue dissolved in dichloromethane and washed with 4% sodium bicarbonate, dried and evaporated to give the title compound (0.68 g) as an oil.

Tlc (Ethyl acetate) Rf 0.27; Mass spectrum MH+ 238

EXAMPLE 27
Cyclopropane carboxylic acid [3-(2,3-dihydro-5-fluorobenzofuran-4-yl)propyl]-amide 3-(2,3-Dihydro-5-fluorobenzofuran-4-yl)propylamine hydrochloride (0.27 g) in dichloromethane (5 ml) containing triethylamine (0.5 ml) was cooled in ice. Cyclopropanecarbonyl chloride (0.12 ml) was added and stirring continued at 5° for 2 h and at room temperature for 16 h. The mixture was washed with water and passed through a solid phase extraction cartridge using ethyl acetate/hexane (1:1) to give the title compound as a white solid (0.21 g).

Tlc (ethyl acetateihexane 1:1) Rf 0.25; mass spectrum MH+ 263

We claim:

1. A compound of formula (I)

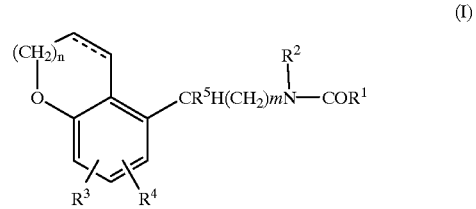

(I)

wherein R¹ and R² which may be the same or different represent H, $C_{1-6}$ alkyl or fluorine substituted alkyl, $C_{3-7}$ cycloalkyl or aryl;

R³, and R⁴ which may be the same or different represent H, halogen, $C_{1-6}$ alkyl; or aryl substituted by one or more groups selected from $C_{1-6}$ alkyl, $C_{1-6}$ alkoxy, hydroxyl, halogen, nitro and trifluoromethyl;

$R^5$ represents H or $C_{1-6}$ alkyl or;

n is an integer 0, 1 or 2;

and m is an integer 1, 2, 3, or 4;

the dotted line indicates the presence or absence of an additional bond; or pharmaceutically acceptable solvate thereof.

2. A compound of formula (Ia)

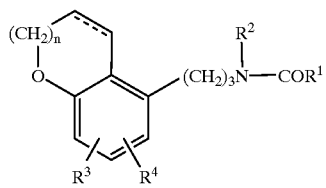

(Ia)

wherein $R^1$ and $R^2$ which may be the same or different represent H, $C_{1-6}$ alkyl or fluorine substituted alkyl, $C_{3-7}$ cycloalkyl or aryl;

$R^3$ and $R^4$ which may be the same or different represent H, halogen or $C_{1-6}$ alkyl;

n is an integer 0, 1 or 2;

the dotted line indicates the presence or absence of an additional bond; or pharmaceutically acceptable solvate thereof.

3. A compound according to claim 1 or 2 wherein $R^3$ and $R^4$ are hydrogen, halogen or $C_{1-3}$ alkyl.

4. A compound according to claim 3 wherein the halogen is chlorine or fluorine.

5. A compound according to claim 1 or 2 wherein $R^1$ and $R^2$ are hydrogen, $C_{1-3}$ alkyl or $C_{3-5}$ cycloalkyl.

6. A compound according to claim 5 wherein $R^1$ is methyl or cyclopropyl.

7. A compound according to claim 6 wherein at least one of $R^1$ and $R^2$ is hydrogen.

8. A compound according to claim 1 wherein n is zero.

9. A compound of formula 1(b)

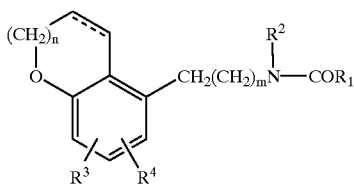

(1b)

wherein $R^1$ and $R^2$ which may be the same or different represent H, $C_{1-6}$ alkyl or fluorine substituted alkyl, $C_{3-7}$ cycloalkyl or aryl;

$R^3$, and $R^4$ which may be the same or different represent H, halogen, or $C_{1-6}$ alkyl or aryl substituted by one or more groups selected from $C_{1-6}$alkyl, $C_{1-6}$alkoxy, hydroxyl, halogen, nitro and trifluoromethyl;

n is an integer 0, or 1;

and m is an integer 2, 3, 4 or 5;

the dotted line indicates the presence or absence of an additional bond; or pharmaceutically acceptable solvate thereof.

10. A compound of formula 1(c)

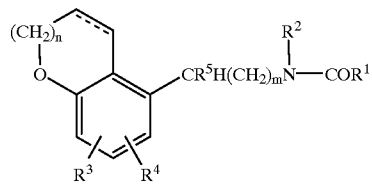

(Ic)

wherein $R^1$ and $R^2$ which may be the same or different represent H, $C_{1-6}$ alkyl or $C_{3-7}$ cycloalkyl;

$R^3$, and $R^4$ which may be the same or different represent H, halogen, or $C_{1-6}$ alkyl;

$R^5$ is H or $C_{1-6}$ alkyl;

n is an integer 0, or 1;

and m is an integer 1, 2, 3, or 4;

the dotted line indicates the presence or absence of an a additional bond; or pharmaceutically acceptable solvate thereof.

11. N-[3-(2,3-dihydro-benzofuran-4-yl)-propyl] acetamide,

Cyclopropanecarboxylic acid -[3-(2,3-dihydro-benzofuran-4-yl)-propyl]-amide,

Cyclopropanecarboxylic acid -[3-(5-chloro-2,3-dihydro-benzofuran-4-yl)propyl]amide, Cyclopropanecarboxylic acid -[3-(5-chloro-7 fluoro-2,3-dihydro-benzofuran-4-yl)propyl]-amide, Cyclopropanecarboxylic acid [3-(5-chloro-7-fluoro-benzofuran-4-yl)-propyl]-amide, Cyclopropanecarboxylic acid -[3-benzofuran-4-yl)-propyl]-amide, Cyclopropanecarboxylic acid (3-chroman-5-yl-propyl)-amide, N-[3-(2,3-dihydro-5-fluorobenzofuran-4-yl)propyl] acetamide, or Cyclopropane carboxylic acid [3-(2,3-dihydro-5-benzofuran-4-yl)propyl]amide.

12. A pharmaceutical formulation comprising a compound of formula (I) according to claim 1 together with one or more pharmaceutically acceptable carriers therefor.

13. A method of treating a mammal of conditions associated with a disturbed functioning of systems regulated by melatonin comprising administration of an effective amount of a compound of formula (I) according to claim 1.

14. The method of claim 13 wherein the mammal is man.

15. A process for the preparation of a compound of formula (I) according to claim 1 which process comprises (A) acylation of a compound of formula (II)

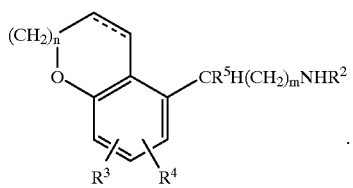

(II)

(B) cyclisation of a compound of formula (XI)

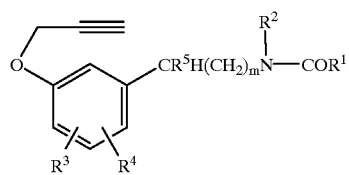

(XI)

16. A process of preparing a pharmaceutical formulation comprising a compound of formula (I) according to claim 1 together with one or more pharmaceutically acceptable carriers therefor, which process comprises mixing said compound of formula (I) together with said one or more pharmaceutically acceptable carriers therefor.

* * * * *